United States Patent
Kohara

(10) Patent No.: US 9,119,560 B2
(45) Date of Patent: Sep. 1, 2015

(54) X-RAY CT APPARATUS

(75) Inventor: Ryota Kohara, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 310 days.

(21) Appl. No.: 13/819,196

(22) PCT Filed: Sep. 1, 2011

(86) PCT No.: PCT/JP2011/069910
§ 371 (c)(1),
(2), (4) Date: Feb. 26, 2013

(87) PCT Pub. No.: WO2012/033002
PCT Pub. Date: Mar. 15, 2012

(65) Prior Publication Data
US 2013/0156149 A1   Jun. 20, 2013

(30) Foreign Application Priority Data
Sep. 7, 2010  (JP) .................................. 2010-199516

(51) Int. Cl.
*A61B 6/00* (2006.01)
*A61B 6/10* (2006.01)
*A61B 6/03* (2006.01)
*G06T 11/00* (2006.01)

(52) U.S. Cl.
CPC . *A61B 6/10* (2013.01); *A61B 6/032* (2013.01); *A61B 6/4078* (2013.01); *A61B 6/461* (2013.01); *A61B 6/5205* (2013.01); *G06T 11/005* (2013.01)

(58) Field of Classification Search
CPC .......... A61B 6/10; A61B 6/032; A61B 6/461; A61B 6/4078; A61B 6/5205; G06T 11/003; G06T 11/005; G06T 11/006; A61N 5/103; A61N 5/1042; A61N 5/1048
USPC ....................................................... 378/4, 901
See application file for complete search history.

(56) References Cited

U.S. PATENT DOCUMENTS

| | | | | |
|---|---|---|---|---|
| 4,670,892 A * | 6/1987 | Abele et al. ........................ | 378/4 |
| 2004/0228434 A1* | 11/2004 | Tsujii ................. | 378/4 |
| 2006/0256920 A1* | 11/2006 | Tsujii ........................... | 378/114 |
| 2007/0195930 A1* | 8/2007 | Kapatoes et al. ............... | 378/65 |
| 2008/0031406 A1* | 2/2008 | Yan et al. ......................... | 378/14 |
| 2009/0141854 A1* | 6/2009 | Hirokawa et al. ................. | 378/4 |

FOREIGN PATENT DOCUMENTS

| | | |
|---|---|---|
| JP | 2005-143759 | 6/2005 |
| JP | 2010-269048 | 12/2010 |

OTHER PUBLICATIONS

Chen et al., Dose-guided radiation therapy with megavoltage cone-beam CT, The British Journal of Radiology, Special Issue, Sep. 2006, vol. 79, p. S87-S95.*
International Search Report in PCT/JP2011/069910.

* cited by examiner

*Primary Examiner* — Irakli Kiknadze
*Assistant Examiner* — Julio M Duarte-Carvajalino
(74) *Attorney, Agent, or Firm* — Cooper & Dunham LLP

(57) ABSTRACT

An X-ray CT apparatus of the present invention includes an image reconstruction unit that, according to scanning conditions, acquires an irradiated X-ray image which is the distribution of the irradiation intensity of X-rays irradiated to an object by an X-ray irradiation unit, performs projection conversion of the irradiated X-ray image and a reconstructed image, and generates an exposure dose image, which is an image showing the distribution of an exposure dose of the object, and also calculates the exposure dose using the projection-converted reconstructed image and an irradiated X-ray image corresponding to a generation region of the reconstructed image.

17 Claims, 12 Drawing Sheets

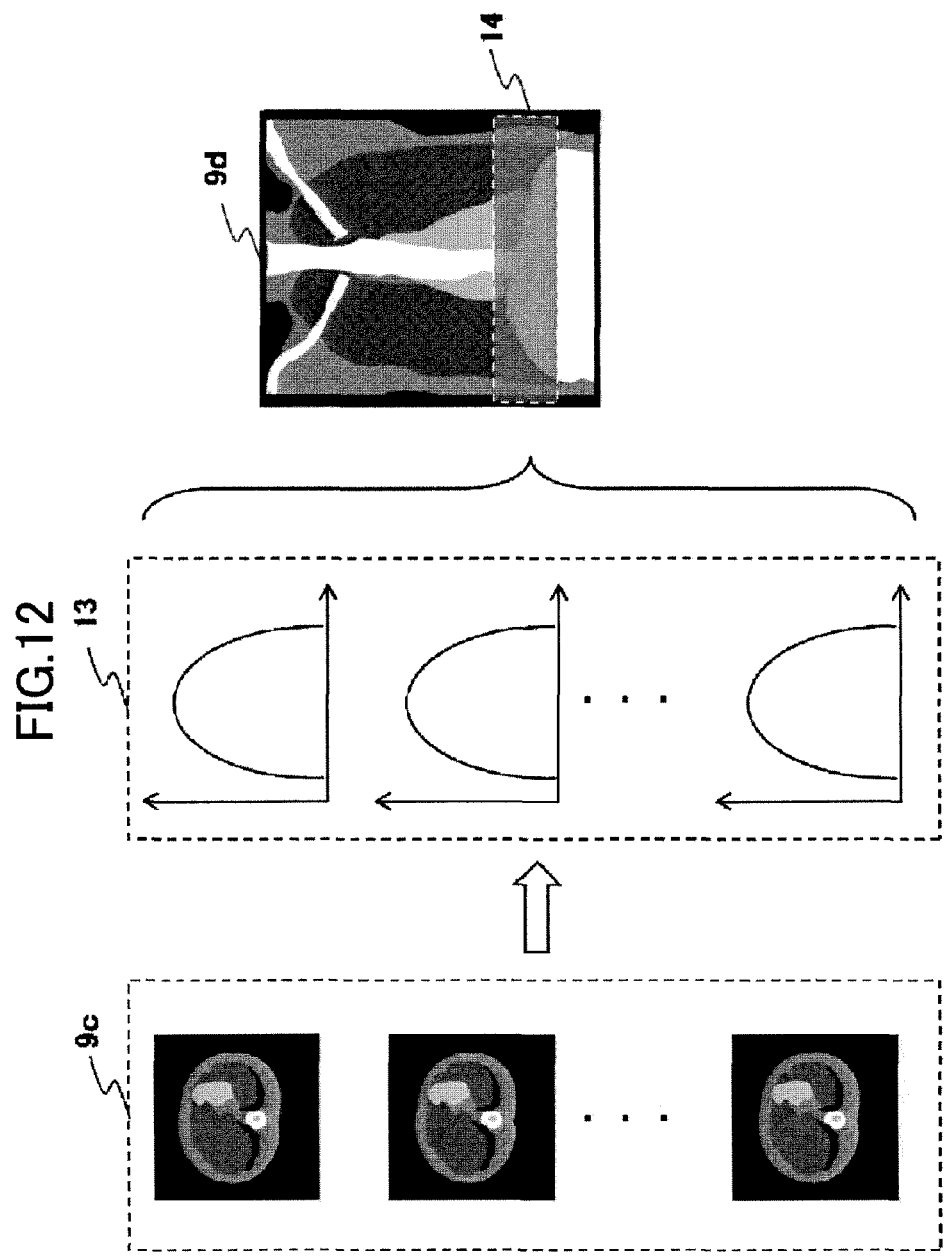

X-RAY CT APPARATUS

TECHNICAL FIELD

The present invention relates to an X-ray CT apparatus that acquires an X-ray CT by irradiating an object with X-rays and in particular, to a technique for measuring an irradiation dose to an object and an exposure dose of the object.

BACKGROUND ART

International Commission on Radiological Protection (ICRP) has advised about "Protecting people and the environment from the harmful effects of radiation exposure at the appropriate level without unduly limiting the activities involving radiation exposure" in 2007. Application of the ICRP recommendations to medical X-ray exposure in image diagnosis has been recommended.

For the application to medical X-ray exposure, it is necessary to measure the X-ray exposure dose. In PTL 1, information regarding the exposure dose when irradiating a predetermined amount of X-rays for a predetermined period of time is stored in a storing unit, an approximately fixed dose of X-rays reaching each part of the object corresponding to each position in a reconstructed X-ray tomographic image is calculated by an X-ray dose calculation unit, and the exposure dose distribution of the object due to X-rays irradiated when reconstructing the X-ray tomographic image is calculated by an exposure dose distribution calculation unit on the basis of the information regarding the exposure dose, the calculated dose of X-rays reaching each part, and the X-ray irradiation time. Accordingly, the exposure dose distribution for each part of the object is calculated.

CITATION LIST

Patent Literature

[PTL 1] JP-A-2005-74000

SUMMARY OF INVENTION

Technical Problem

In PTL 1, however, the exposure dose is calculated on the basis of the approximately fixed irradiation dose. For this reason, as the number of regions having different CT values in a CT tomographic image, such as an organ or tissue, increases, the amount of calculation related to the exposure dose calculation increases.

Therefore, since the calculation processing time for the exposure dose calculation becomes long, there still remains a problem to be solved that it takes time to evaluate the exposure dose of the object.

It is an object of the present invention to provide an X-ray CT apparatus capable of quickly evaluating the exposure dose of an object.

Solution to Problem

In order to achieve the above-described object, the present invention includes an image reconstruction unit that, according to scanning conditions, acquires an irradiated X-ray image which is a distribution of an irradiation intensity of X-rays irradiated to an object by an X-ray irradiation unit, performs projection conversion of the irradiated X-ray image and a reconstructed image, and generates an exposure dose image, which is an image showing a distribution of an exposure dose of the object, and also calculates the exposure dose using the projection-converted reconstructed image and an irradiated X-ray image corresponding to a generation region of the reconstructed image.

Advantageous Effects of Invention

According to the present invention, the exposure dose of the object can be quickly evaluated.

BRIEF DESCRIPTION OF DRAWINGS

FIG. 12 is a diagram for explaining cumulative exposure dose image generation processing in a fourth embodiment.

DESCRIPTION OF EMBODIMENTS

Hereinafter, preferred embodiments of the present invention will be described in detail with reference to the accompanying drawings. The present invention is for evaluating an exposure dose in the image diagnosis that is performed using an X-ray CT apparatus.

First Embodiment

First, the configuration of an X-ray CT apparatus according to the present invention will be described with reference to FIGS. 1 and 2.

Figure 1:
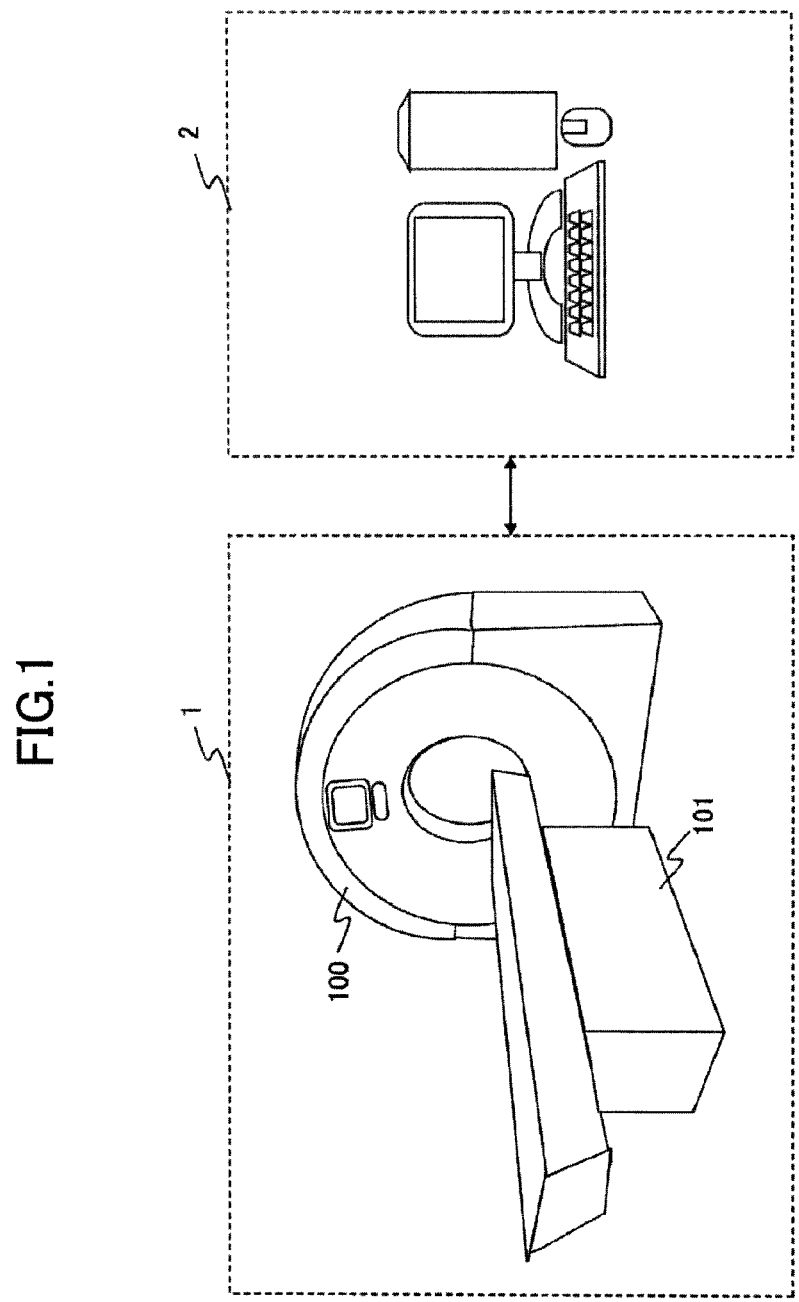
FIG. 1 is a diagram showing the overall configuration of an X-ray CT apparatus.

As shown in FIG. 1, the X-ray CT apparatus is configured to include scanning means 1, operating means 2, and the like. The scanning means 1 includes a gantry 100 having a scanner body inside and a bed 101. The operating means 2 operates and controls the scanning means 1. In addition, the operating means 2 performs input of the scanning conditions, image processing, and the like.

Figure 2:
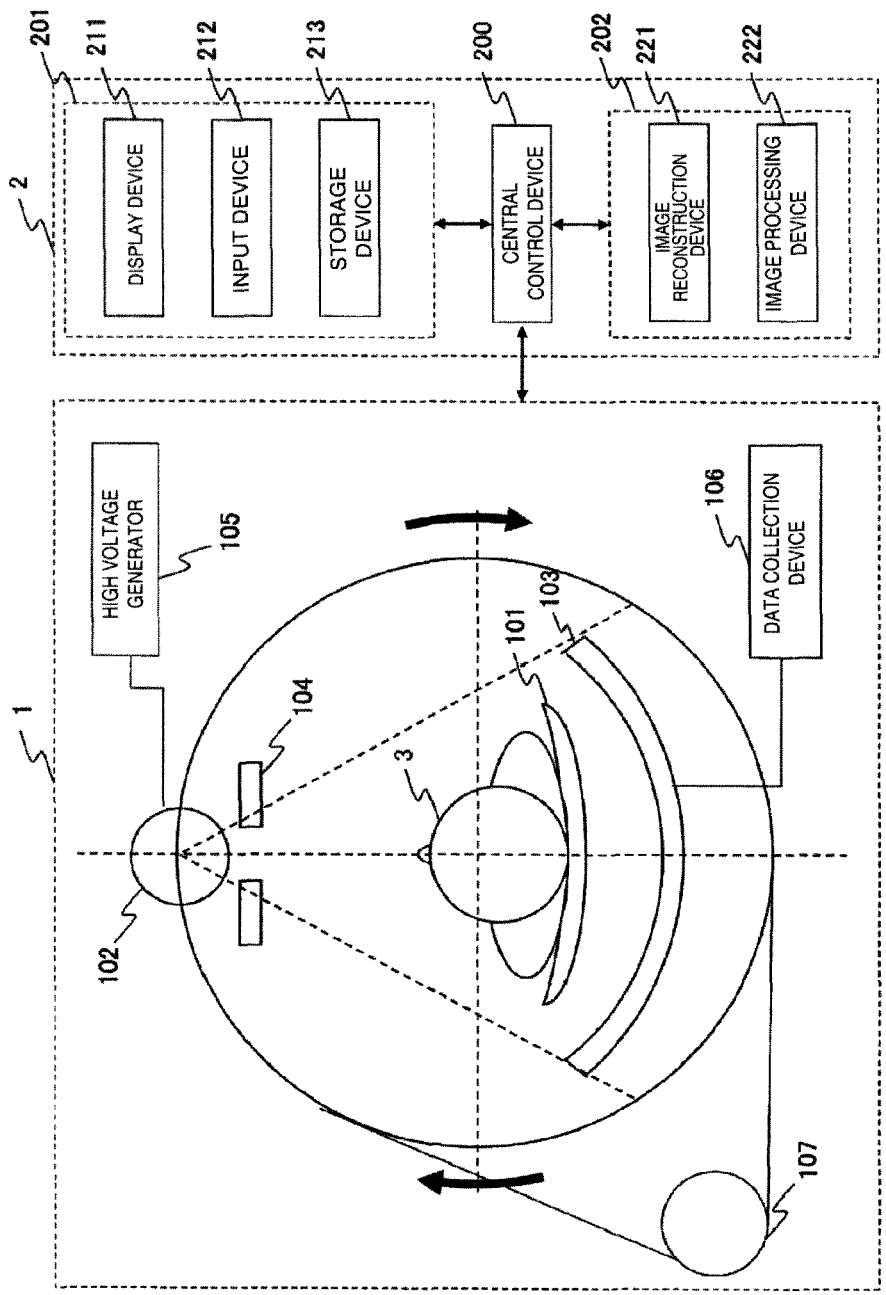
FIG. 2 is a diagram showing components of the X-ray CT apparatus.

As shown in FIG. 2, the gantry 100 is configured to include an X-ray generator 102 that irradiates X-rays from the periphery of an object 3, a collimator device 104 that narrows the range of the X-ray flux generated from the X-ray generator 102, an X-ray detector 103 that detects X-rays transmitted through the object 3, a high voltage generator 105 that applies a high voltage to the X-ray generator 102, a data collection device 106 that collects data detected by the X-ray detector 103, a driving device 107 that rotates a scanner around the object 3, and the like. In addition, the collimator device 104 may include a compensation filter for adjusting the radiation distribution of X-rays and the like.

The operating means 2 is configured to include an input/output device 201, a calculation device 202, a central control device 200, and the like.

The input/output device 201 is configured to include a display device 211 that displays data such as an image, an input device 212 used when an operator inputs scanning conditions and the like, a storage device 213 that stores data required for scanning such as a program and a device parameter, and the like.

The calculation device 202 is configured to include an image reconstruction device 221 that generates a reconstructed image of the object 3 on the basis of the data obtained from the scanning means 1, an image processing device 222 that performs analysis of image data, and the like. The central control device 200 controls each device of the scanning means 1 and the operating means 2 according to the instructions based on the operation of the operator.

As scanning using an X-ray CT apparatus, there are rotation scanning in which scanning is performed while the X-ray generator 102 and the data collection device 106 are rotating within the gantry 100 and stationary scanning in which scanning is performed in a state where the X-ray generator 102 and the data collection device 106 remain stationary within the gantry 100. Tomographic scanning for obtaining a tomographic image of the object 3 is based on rotation scanning. In addition, scanogram imaging for determining the scanning position of tomographic scanning is based on the stationary scanning. In addition, the scanning trajectory of tomographic scanning may be any of a circular trajectory, a spiral trajectory, and a combination of a circular trajectory and a spiral trajectory, and is not particularly limited.

Here, the X-ray CT apparatus including the scanning means 1 and the operating means 2 shown in FIGS. 1 and 2 can be regarded as an X-ray CT apparatus in which devices, such as a display device and an input/output device provided in the X-ray CT apparatus, are electrically connected to each other through a wire, a network, or the like. In addition, in the case of a data processing apparatus such as a workstation or a desktop computer shown in the operating means 2 of FIG. 1, such an apparatus can be replaced as follows. That is, the input/output device 201 that forms the operating means 2 is an input/output unit, the central control device 200 is a control unit, and the calculation device 202 is a calculation unit. Through such a configuration, such a data processing apparatus has the same configuration as an integrated stand-alone type apparatus.

Similarly, in the scanning means 1 shown in FIG. 1, the X-ray generator 102 is an X-ray generation unit, the collimator device 104 is a collimator unit, the X-ray generation unit and the collimator unit form an X-ray irradiation unit, the X-ray detector 103 is an X-ray detection unit, the high voltage generator 105 is a high voltage generation unit, the data collection device 106 is a data collection unit, and the driving device 107 is a driving unit. That is, the scanning means 1 is configured to include these units, the gantry 100, and the bed 101. Each unit of the scanning means 1 and the operating means 2 has the same function as the device described above.

In addition, the "X-ray irradiation unit", the "X-ray detection unit", the "image reconstruction unit", and the "display unit" are defined as follows.

The "X-ray irradiation unit" irradiates X-rays from the periphery of an object, and is configured to include an X-ray generation unit 102 that irradiates X-rays from the periphery of the object 3 and a collimator unit 104 that narrows the range of the X-ray flux generated from the X-ray generation unit 102.

The "X-ray detection unit" detects X-rays transmitted through the object as X-ray information, and the X-ray detector 103 corresponds thereto.

The "image reconstruction unit" generates a reconstructed image of the object from the X-ray information detected by the X-ray detection unit. According to the scanning conditions, the "image reconstruction unit" acquires an irradiated X-ray image that is a distribution of the irradiation intensity of X-rays irradiated to the object by the X-ray irradiation unit, performs projection conversion of the irradiated X-ray image and the reconstructed image, and generates an exposure dose image, which is an image showing the distribution of the exposure dose of the object, or calculates the exposure dose using the projection-converted reconstructed image and the irradiated X-ray image corresponding to the reconstructed image generation region. The image reconstruction device 221 corresponds to the "image reconstruction unit".

The "display unit" displays the exposure dose image and the exposure dose, and the display device 211 corresponds thereto.

In the present embodiment, an image reconstruction unit (image reconstruction device 221) evaluates an exposure dose of the object 3 by executing the flow of processing to be described later.

Here, the definitions of terms are described.

An "image" is not limited to being visibly displayed on the display device, and is assumed to mean a data set of pixel values. In addition, the "generation of an image" means calculating each pixel value.

In addition, when a dose of X-rays (irradiation dose) irradiated to the object 3, a dose of X-rays (exposure dose) indicating the amount of exposure of the object 3, and the like do not need to be distinguished, they are simply described as a "dose".

"Irradiated X-ray information" is the distribution of the irradiation intensity of X-rays irradiated to the object 3 by the X-ray generator 102.

The "irradiated X-ray image" and the "irradiation dose image" are images showing the distribution of the irradiation dose of X-rays irradiated to the object 3.

An "attenuation coefficient image" is an image showing the distribution of an attenuation coefficient.

An "irradiation dose correction image" is an image showing a reduction result of the amount of attenuation with respect to an irradiation dose image. That is, the irradiation dose correction image is an image showing a result after reducing the amount of attenuation, according to the object 3, from the irradiation dose image.

An "absorbed dose image" is an image showing the distribution of the absorbed dose of X-rays absorbed into the object 3. The absorbed dose is the basic amount of dosimetry in radiation protection, and is defined as energy absorbed per unit mass. The unit of absorbed dose is J/kg (special unit is Gy (gray)).

An "equivalent dose image" is an image showing the distribution of an equivalent dose. The equivalent dose is a product of the average absorbed dose and the radiation weighting factor for each organ and tissue. The unit of equivalent dose is J/kg (special unit is Sv (sievert)). In addition, in the recommendations of the ICRP, the radiation weighting factor in the photon is 1 without being limited by the range of energy. Accordingly, in the CT, the absorbed dose and the equivalent dose are the equal.

An "effective dose image" is an image showing an effective dose. The International Commission on Radiological Protection (ICRP) defines the effective dose image as a value obtained by giving the tissue weighting factor, which indicates the different radiosensitivity according to an organ and/or tissue (hereinafter, referred to as an organ or the like), for the equivalent dose and totaling the result for all organs or the like. The unit of effective dose is J/kg (special unit is Sv (sievert)).

The "organ distinction image" is an image for identifying the regions of an organ or the like included in the reconstructed image.

A "tissue weighting factor image" is an image in which the tissue weighting factor is weighted for the equivalent dose image for each region, such as an organ or the like identified by the organ distinction image.

An "exposure dose image" is an image showing the distribution of the exposure dose of the object 3. The exposure dose image is calculated as an effective dose image, for example.

Next, processing of the X-ray CT apparatus in the first embodiment will be described with reference to FIGS. 3 to 7.

Figure 3:
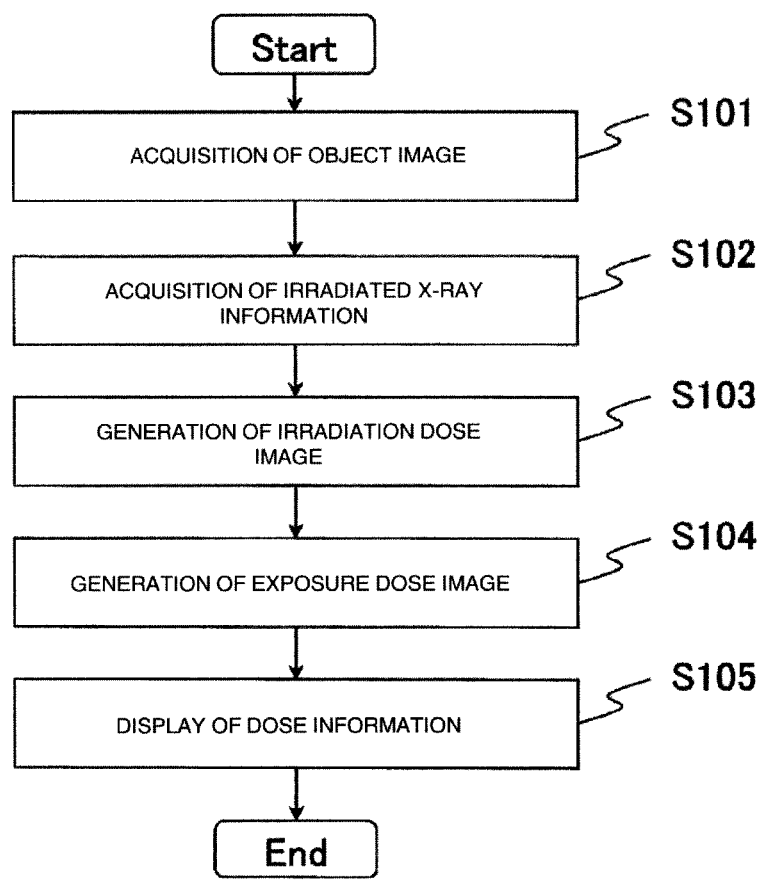
FIG. 3 is a flowchart showing the flow of dose evaluation processing in a first embodiment.

As shown in FIG. 3, the image reconstruction device 221 of the X-ray CT apparatus acquires an object image (S101).

Figure 4:
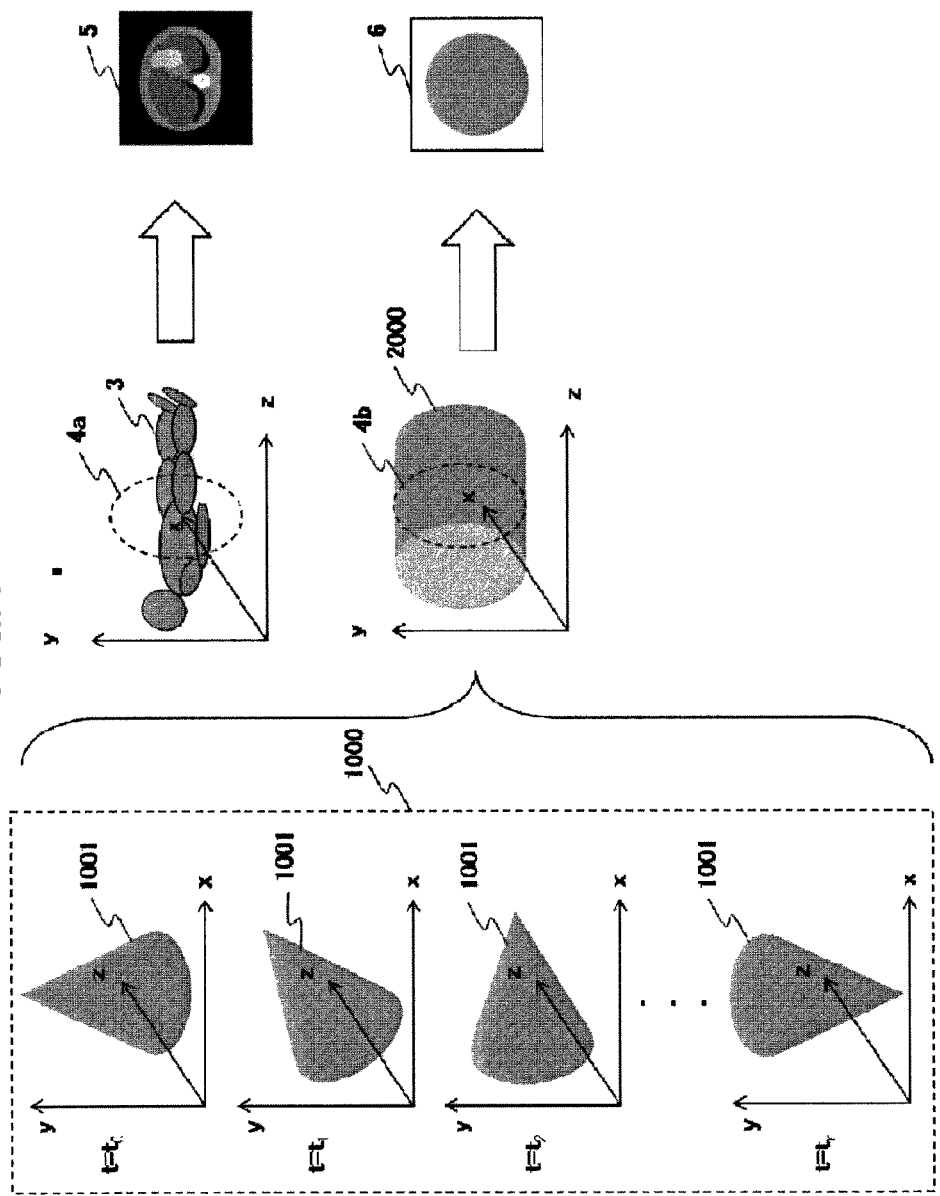
FIG. 4 is a diagram for explaining irradiation dose image generation processing in the first embodiment.

The object image in the first embodiment is a tomographic image 5 (reconstructed image) of the object 3 shown in FIG. 4. The tomographic plane of the tomographic image 5 is a region 4a shown by the dotted line. One or a plurality of tomographic images 5 may be used, and the number of tomographic images 5 is not particularly limited. In addition, the object image in the first embodiment may be not only a cross-sectional image (axial image) perpendicular to the body axis of the object 3, such as the tomographic image 5, but also a cross-sectional image (coronal image) parallel to the body axis of the object 3 and in a lateral direction of the object 3 or a cross-sectional image (sagittal image) parallel to the body axis of the object 3 and in a direction from the front to the rear of the object 3.

Then, the image reconstruction device 221 of the X-ray CT apparatus acquires the irradiated X-ray information from the storage device 213 according to the scanning conditions (S102).

The image reconstruction device 221 acquires the irradiated X-ray information from the storage device 213 at each time (t=t0, . . . , tn) at predetermined intervals from the start (t=t0) of X-ray irradiation to the end (t=tn) of X-ray irradiation. That is, the image reconstruction device 221 acquires the irradiated X-ray information according to the scanning conditions at predetermined intervals (for example, for each view).

The irradiated X-ray information is three-dimensional irradiation intensity distribution data 1001 shown in FIG. 4. The image reconstruction device 221 stores the three-dimensional irradiation intensity distribution data 1001 in the storage device 213 for each scanning condition before S102.

In the example shown in FIG. 4, the three-dimensional irradiation intensity distribution data 1001 has the spread (fan angle) of X-ray beams in the slice surface direction (x-y plane direction) and the spread (cone angle) of X-ray beams in the body axis direction (z-axis direction). However, the three-dimensional irradiation intensity distribution data 1001 is not limited to the example shown in FIG. 4.

The three-dimensional irradiation intensity distribution data 1001 may be any of data measured in advance before the scanning of the tomographic image 5, data obtained during the scanning of the tomographic image 5, and data obtained by a numerical simulation. In addition, the three-dimensional irradiation intensity distribution data 1001 may be data obtained by modeling or parameterizing the measured data or the simulation data.

The three-dimensional irradiation intensity distribution data 1001 changes with voltage and current (tube voltage and tube current) which are applied to the X-ray generator 102. In addition, the three-dimensional irradiation intensity distribution data 1001 also changes with the degree of the opening of the collimator unit of the collimator device 104. In addition, the three-dimensional irradiation intensity distribution data 1001 also changes with the geometric characteristics of the gantry 100. The three-dimensional irradiation intensity distribution data 1001 may be defined according to various scanning conditions without limiting the scanning conditions in particular.

Explanation continues referring back to FIG. 3. Then, the image reconstruction device 221 of the X-ray CT apparatus generates a irradiation dose image (S103).

The image reconstruction device 221 generates three-dimensional irradiation dose data 2000 by performing time integration of a group 1000 of the plurality of three-dimensional irradiation intensity distribution data items acquired in S102. The three-dimensional irradiation dose data 2000 is a sum of the dose of X-rays irradiated from the start (t=t0) of X-ray irradiation to the end (t=tn) of X-ray irradiation. In addition, the image reconstruction device 221 sets a reconstructed image generation region, that is, a region 4b present at the same z position as the generation region 4a showing the tomographic plane of the tomographic image 5, as a cut plane, and extracts the pixel value of the three-dimensional irradiation dose data 2000 in the cut plane and sets the result as a irradiation dose image 6.

In addition, the irradiation dose image 6 shown in FIG. 4 is expressed such that the pixel value of the circular region is fixed, but each pixel has a different pixel value in practice. That is, the irradiation dose image 6 is an image with distribution.

As shown in FIG. 4, the region of the three-dimensional irradiation dose data 2000 is a cylindrical shape extending from the minimum Z position, at which X-rays arrive, in the body axis direction (z-axis direction) to the maximum Z position (the maximum and minimum positions are determined by the scanning start position and the scanning end position, respectively) with the inner peripheral surface of the gantry 100 (opening of the gantry 100) as across-section, for example. However, the shape of the region of the three-dimensional irradiation dose data 2000 is not limited to this, and at least the irradiation range of X-rays that may be irradiated to the object 3 at the time of scanning is preferably included. For example, the cross-section of the region of the three-dimensional irradiation dose data 2000 is not limited to a circle, and may be a shape such as an ellipse or a rectangle. In addition, the cross-section of the region of the three-dimensional irradiation dose data 2000 may have an area changing in the body axis direction (z-axis direction).

Explanation continues referring back to FIG. 3. Then, the image reconstruction device 221 of the X-ray CT apparatus generates an exposure dose image (S104).

Hereinafter, exposure dose image generation processing will be described with reference to FIGS. 5 and 6.

Figure 5:
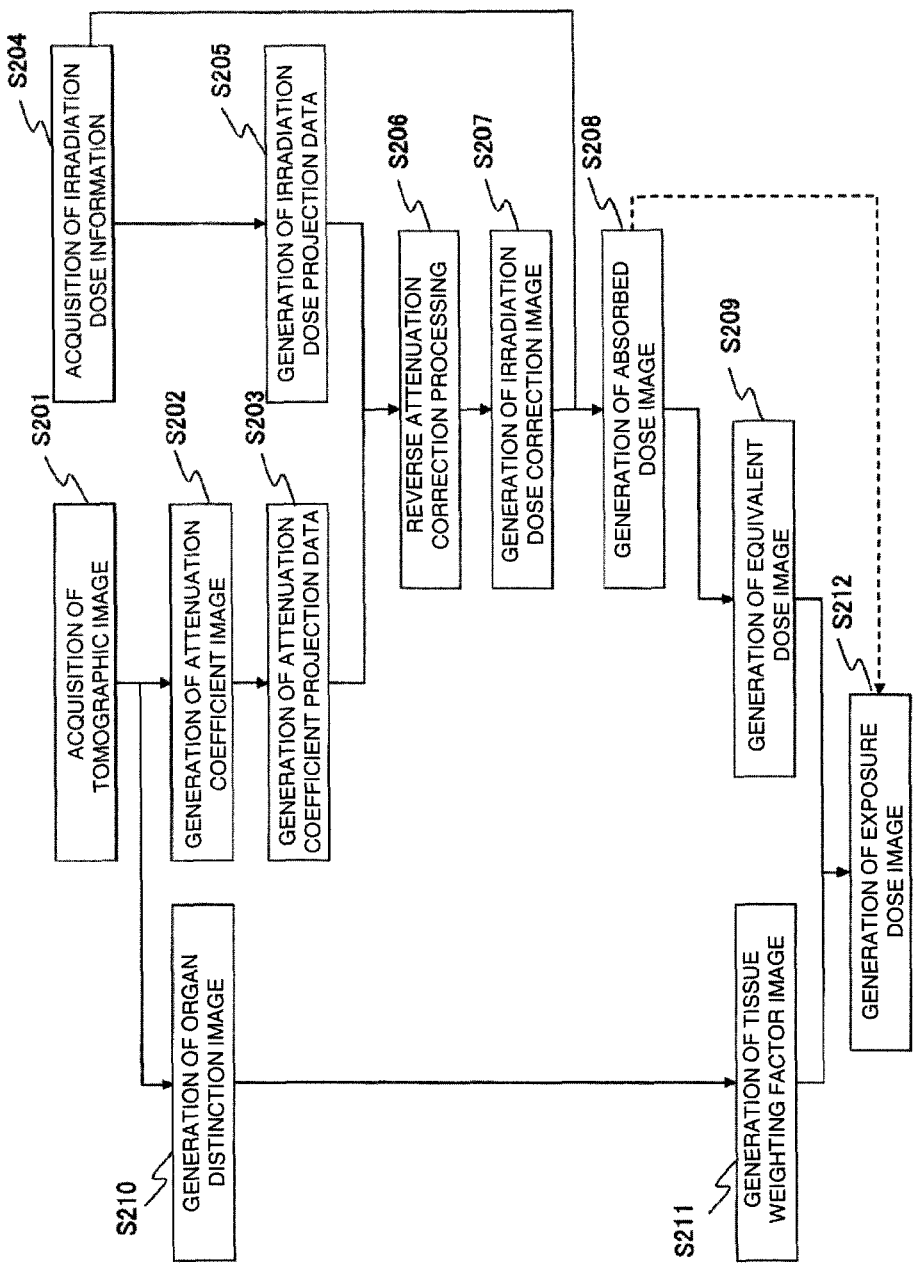
FIG. 5 is a flow chart showing the flow of exposure dose image generation processing in the first embodiment.
Figure 6:
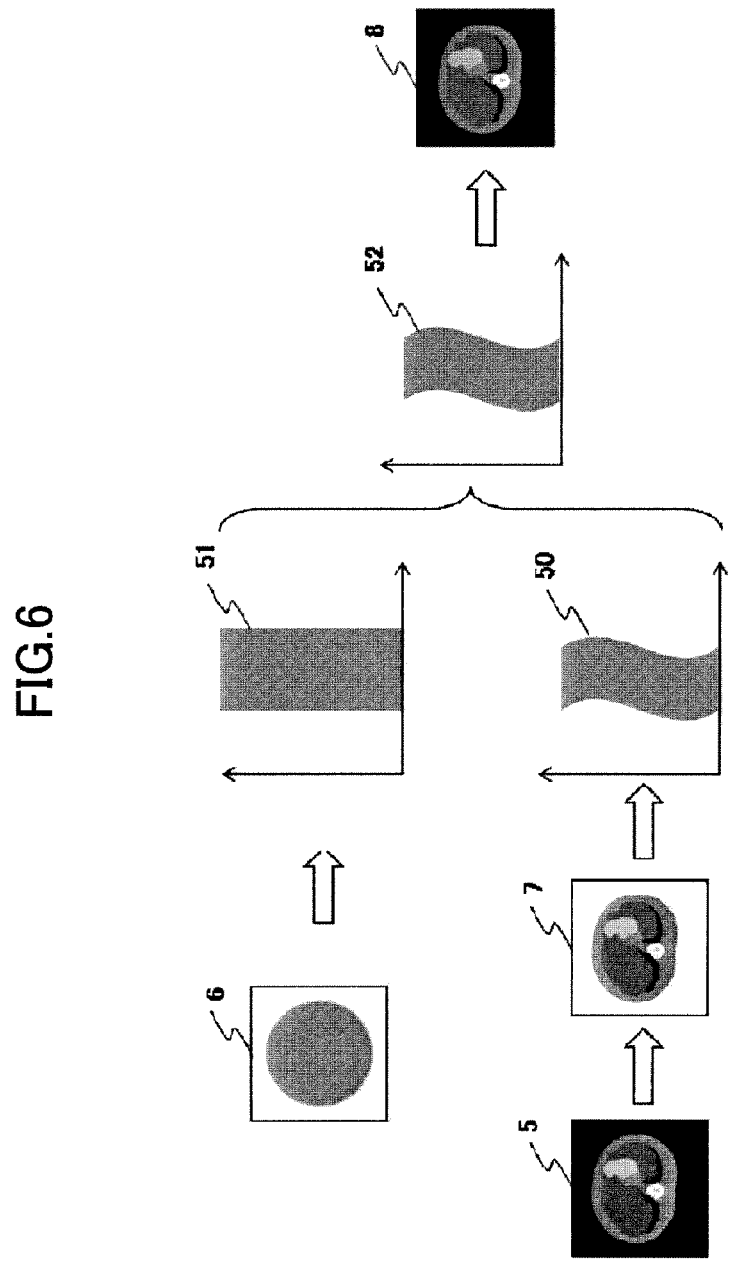
FIG. 6 is a diagram for explaining exposure dose image generation processing in the first embodiment.

As shown in FIG. 5, the image reconstruction device 221 acquires the tomographic image 5 shown in FIG. 4 (S201), and converts the tomographic image 5 into an attenuation coefficient image 7 on the basis of information indicating the relationship between the CT value and the linear attenuation coefficient (S202).

The relationship between the CT value and the linear attenuation coefficient is expressed by the relational expression of "CT value=(μt−μw)/μw×k" (μt: linear attenuation coefficient of the object 3, μw: linear attenuation coefficient of water, K: constant).

The linear attenuation coefficient is a physical coefficient determined by the energy distribution of irradiated X-rays and materials which form the object 3. The information (conversion data for converting the CT value into the attenuation coefficient) indicating the relationship between the CT value and the attenuation coefficient depends on the scanning conditions, the characteristics of the X-ray CT apparatus, and the like. The conversion data may be data measured in advance before the scanning of the tomographic image 5 or data obtained by a numerical simulation, or may be data obtained by modeling or parameterizing the measured data or the simulation data.

Then, the image reconstruction device 221 converts the attenuation coefficient image 7 into attenuation coefficient projection data 50 by performing forward projection (also referred to as re-projection) processing (S203). Here, the forward projection processing is a process for conversion (so-called radon conversion) from the distribution of the linear attenuation coefficient in the Cartesian coordinate system to the distribution of the linear attenuation coefficient in the projection coordinate system. The Cartesian coordinate system is a coordinate system in which the object 3 is fixed. The projection coordinate system is a coordinate system showing the position when the X-ray generator 102 and the data collection device 106 rotate by θ with respect to the Cartesian coordinate system.

Then, the image reconstruction device 221 acquires the irradiation dose image 6 generated in S103 of FIG. 3 (S204), and converts the irradiation dose image 6 into irradiation dose projection data 51 by performing forward projection processing (S205). The forward projection processing in S205 is the same as the forward projection processing in S203.

Then, an exposure dose image which is an image showing the distribution of the exposure dose of the object is generated using a reconstructed image and an irradiated X-ray image corresponding to the reconstructed image generation region. That is, the image reconstruction device 221 performs reverse attenuation correction processing on the irradiation dose projection data 51 using the attenuation coefficient projection data 50 (S206). Specifically, the image reconstruction device 221 generates attenuation correction irradiation dose projection data 52 using the expression (1) shown below.

[Expression 1]

$$g_E(X,\theta)=e^{-g_T(X,\theta)}g_0(X,\theta) \quad (1)$$

$g_E(X,\theta)$: attenuation correction irradiation dose projection data
$g_T(X,\theta)$: attenuation coefficient projection data
$g_0(X,\theta)$: irradiation dose projection data Normal attenuation correction has the effect of undoing the amount of attenuation with respect to the data to be corrected (normally, data indicating the dose of X-rays transmitted through the object 3). On the other hand, since the processing of S206 has the effect of reducing the amount of attenuation with respect to the data to be corrected (in S206, data indicating the dose of X-rays irradiated to the object 3), the processing of S206 is called "reverse" attenuation correction.

In addition, in the reverse attenuation correction processing of S206, it is possible to add a correction that takes into consideration the influence of diffusion, refraction, and diffraction of X-rays by the object 3 or the directivity of X-rays.

Then, the image reconstruction device 221 generates a irradiation dose correction image 8 by performing reverse projection processing of the attenuation correction irradiation dose projection data 52 (S207). Here, the reverse projection processing is a process for conversion (so-called reverse radon conversion) from the distribution of the linear attenuation coefficient in the projection coordinate system to the distribution of the linear attenuation coefficient in the Cartesian coordinate system.

Essential information for evaluating the exposure of the object 3 is included in the irradiation dose correction image 8. S208 and S209, which will be described later, are processing for converting the irradiation dose correction image 8 in the existing dose unit.

Then, the image reconstruction device 221 calculates a difference between the irradiation dose image 6 and the irradiation dose correction image 8, and generates an absorbed dose image on the basis of the calculated difference (S208). The difference between the irradiation dose image 6 and the irradiation dose correction image 8 indicates the amount of attenuation by the object 3. In the present invention, it is assumed that the amount of attenuation by the object 3 is equivalent to the absorbed dose of the object 3. Similar to the irradiation dose image 6, the absorbed dose image is also an image with distribution.

Then, the image reconstruction device 221 generates an equivalent dose image by multiplying the absorbed dose image by the radiation weighting factor (S209). As defined above, since the radiation weighting factor in the photon is 1 without being limited to the range of energy in the recommendations of the ICRP, the absorbed dose image and the equivalent dose image are equal.

Then, the image reconstruction device 221 generates an organ distinction image by performing region determination on the basis of the CT value of the tomographic image 5 and identifying the region of an organ or the like (S210). The organ distinction image is a map of an organ or the like, and is a label image obtained by attaching different labels to organs or the like, for example.

In addition, the region determination may be performed on the basis of the features of the anatomical shapes of organs or the like instead of the CT value.

In addition, the image reconstruction device 221 may identify parts of the human body instead of identifying the region of an organ or the like, and generate an image of each part.

Then, the image reconstruction device 221 generates a tissue weighting factor image using the tissue weighting factor corresponding to the organ or the like (S211). As the tissue weighting factor, for example, the value shown in the recommendations of the ICRP may be used.

In addition, the image reconstruction unit calculates an exposure dose. That is, the image reconstruction device 221 generates a tissue weighting factor image by collating the organ distinction image with the equivalent dose image (or the absorbed dose image). The tissue weighting factor image shows a calculation result of the exposure dose of each organ or the like. It is possible to evaluate the exposure dose for each organ or the like of the object 3 due to the tissue weighting factor image.

In addition, the image reconstruction device 221 generates a part weighting factor image by collating the image according to a part image with the equivalent dose image (or the absorbed dose image). The part weighting factor image shows a calculation result of the exposure dose for each part (head, a chest, abdomen, limbs, or the like) of the human body.

Then, the image reconstruction device 221 converts the equivalent dose image into an effective dose image using the tissue weighting factor image, and sets the effective dose image as an exposure dose image (S212). As defined above, the effective dose image is an image obtained by weighting an equivalent dose image with a tissue weighting factor.

In addition, the image reconstruction device 221 may convert the absorbed dose image into the exposure dose image using a dose equivalent conversion factor. For example, the value shown in the recommendations of the ICRP may be used as the dose equivalent conversion factor.

Explanation continues referring back to FIG. 3. Then, the display device 211 of the X-ray CT apparatus displays the dose information (S105).

Hereinafter, a display example of the dose information will be described with reference to FIG. 7.

Figure 7:
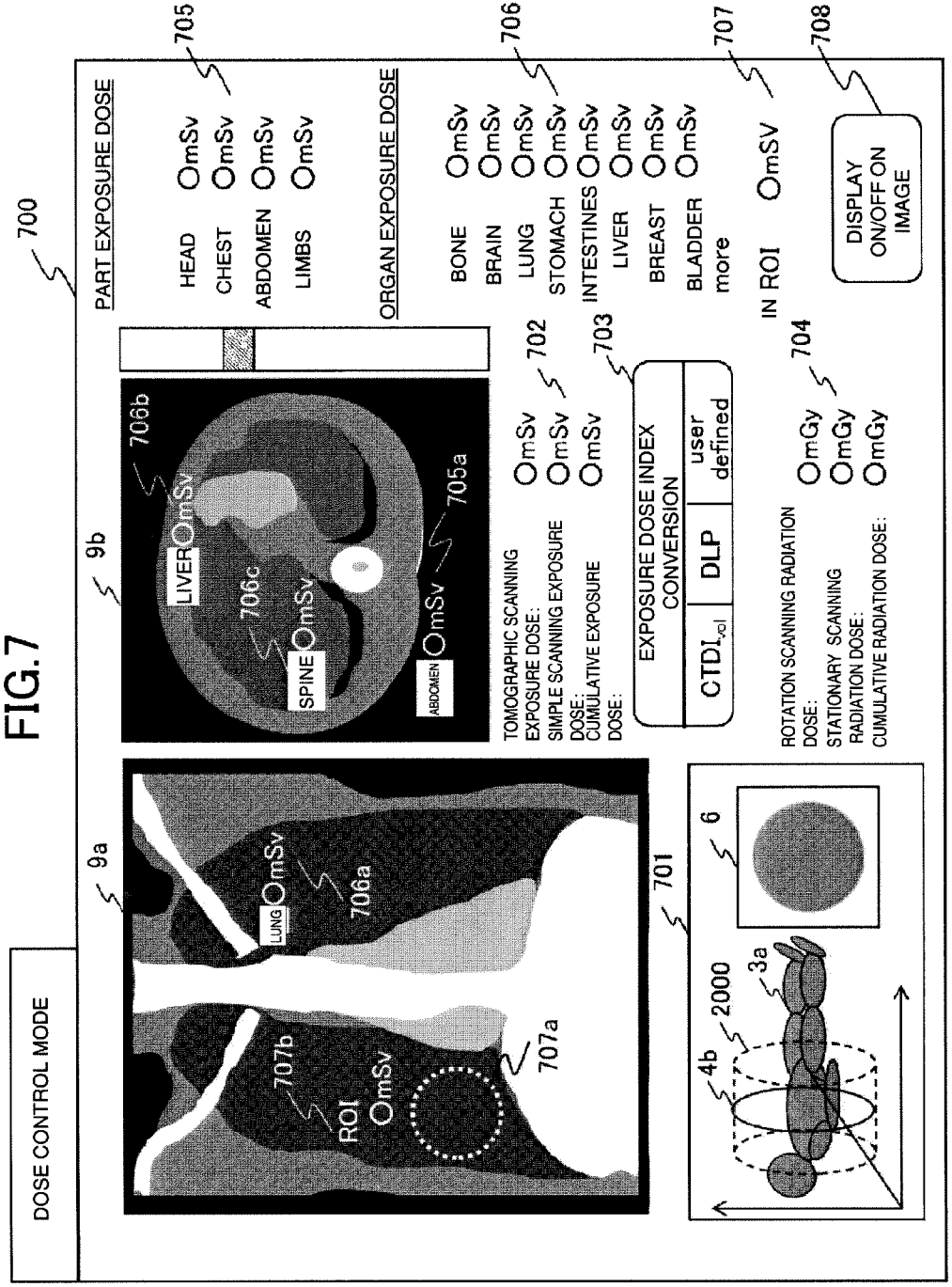
FIG. 7 is a diagram showing an example of a screen on which dose evaluation information is displayed.

As shown in FIG. 7, the display device 211 displays a dose management screen 700 on the basis of the calculation result of the image reconstruction device 221.

In the dose management screen 700 shown in FIG. 7, an exposure dose image 9a of a coronal image, an exposure dose image 9b of an axial image, an irradiation range image 701 obtained by overlapping the irradiation dose image 6 on a virtual image 3a of the object 3, an exposure dose 702 according to scanning, an exposure dose index conversion button 703, a irradiation dose 704 according to scanning, an exposure dose 705 according to a part, an exposure dose 706 according to an organ, an exposure dose 707 in an ROI (region of interest), and an ON/OFF button 708 of a display on an image are included.

When a display on an image becomes ON due to the ON/OFF button 708 of a display on an image, some information of the exposure dose 705 according to a part, the exposure dose 706 according to an organ, and the exposure dose 707 in an ROI is displayed in the exposure dose images 9a and 9b.

An exposure dose 706a of the lung, an ROI 707a, and an exposure dose 707b in the ROI are displayed in the exposure dose image 9a so as to overlap each other. In addition, an exposure dose 705a of the abdomen, an exposure dose 706b of the liver, and an exposure dose 706c of the spine are displayed in the exposure dose image 9b so as to overlap each other.

Not only the virtual image 3a of the object 3 and the irradiation dose image 6 but also the cylindrical three-dimensional irradiation dose data 2000 and the circular region 4b showing the cut plane of the irradiation dose image 6 are displayed in the irradiation range image 701.

Through the irradiation range image 701, the user can roughly check the irradiation range of X-rays for the object 3.

An exposure dose from tomographic scanning, an exposure dose from simple scanning (scanogram imaging), and a cumulative exposure dose from tomographic scanning and simple scanning are displayed in the exposure dose 702 according to scanning. In addition, the calculation of the exposure dose from simple scanning or the cumulative exposure dose from tomographic scanning and simple scanning will be described later in a subsequent embodiment.

The exposure dose index conversion button 703 is a button for converting the index of the exposure dose into other indices. As other indices, existing indices, such as a CTDI (Computed Tomography Dose Index), a DLP (Dse Length Product), a CTDIw (weighted CTDI), and CTDIvol (volumetric CTDI), or user-defined indices may be considered. The image reconstruction device 221 calculates the CTDI, the DLP, the CTDIw, and the CTDIvol on the basis of the irradiation dose image 6.

A irradiation dose from rotation scanning (equivalent to tomographic scanning), a irradiation dose from stationary scanning (equivalent to scanogram imaging), and a cumulative irradiation dose from rotation scanning and stationary scanning are displayed in the irradiation dose 704 according to scanning. In addition, the calculation of the exposure dose from stationary scanning or the cumulative irradiation dose from rotation scanning and stationary scanning will be described later in a subsequent embodiment.

Exposure doses of the head, chest, abdomen, and limbs are displayed in the exposure dose 705 according to a part.

Exposed doses of the bone, brain, lung, stomach, intestines, liver, breast, bladder, and the like are displayed in the exposure dose 706 according to an organ.

An exposure dose in the ROI is displayed in the exposure dose 707 in an ROI.

As described above, according to the first embodiment, the exposure dose of the object 3 and the irradiation dose for the object 3 according to the scanning conditions can be quickly evaluated in the tomographic scanning (rotation scanning).

In addition, the exposure dose of the object 3 and the irradiation dose for the object 3 can be quickly evaluated and managed with high accuracy and in detail.

In the present invention, the physical characteristics reflecting the material configuration of the object 3 and the morphological information included in the reconstructed image (clinical image information) are used. Accordingly, the present invention can be applied to a CT tomographic image in which different things from body tissue, such as things remaining in the body or a contrast agent, or things which significantly attenuate irradiated X-rays are present as the object 3, or can be applied to a CT tomographic image on which an scanning method is performed so as to modulate the intensity or energy of irradiated X-rays at short intervals during scanning. As a result, it is possible to evaluate the exposure dose of the object.

In addition, since only the morphological information and the physical characteristics are referred to from the reconstructed image, it is possible to evaluate the exposure dose even in the case of a reconstructed image on which an image reconstruction method or an image processing method to change the image characteristics has been performed.

In addition, since a irradiation dose image can be provided, it is also possible to evaluate and manage the irradiation dose. Accordingly, conversion into the indices (CTDI, DLP, CTDIw, CTDIvol, and the like) of the exposure dose unique to the known CT examination can be easily performed.

In particular, due to the processing shown in S201 to S207 shown in FIG. 5, the three-dimensional distribution of the amount of irradiated X-rays is taken into consideration for each pixel in an image to evaluate the exposure dose. Accordingly, since it is possible to calculate the amount of attenuation when the shape of the object 3 in each X-ray irradiation direction is taken into consideration, the exposure dose of the object 3 can be evaluated with high accuracy.

In addition, in the processing shown in S201 to S207 shown in FIG. 5, calculation processing for each organ or the like of the object 3 (for example, processing for calculating the transmission length of an X-ray for each organ or the like) is not performed. Accordingly, since the amount of calculation is reduced even if many organs or the like are present in the image to evaluate the exposure dose, it is possible to shorten the calculation time.

In addition, using the value shown in the recommendations of the ICRP in S210 to S211 shown in FIG. 5, it is possible to calculate an exposure dose for each organ or the like. This is based on the fact that the absorbed dose can be calculated in pixel units with high accuracy by the processing shown in S201 to S207 shown in FIG. 5.

Second Embodiment

Although the evaluation of the exposure dose by tomographic scanning (rotation scanning) has been described in the first embodiment, the evaluation of the exposure dose by scanogram imaging (stationary scanning) will be described in a second embodiment.

The scanogram imaging is stationary scanning and is scanning for obtaining a scanogram image (dynamic image through which the movement of an organ or the like of the object 3 can be checked) of the object 3.

Processing of an X-ray CT apparatus in the second embodiment will be described with reference to FIGS. 8 to 10.

Figure 8:
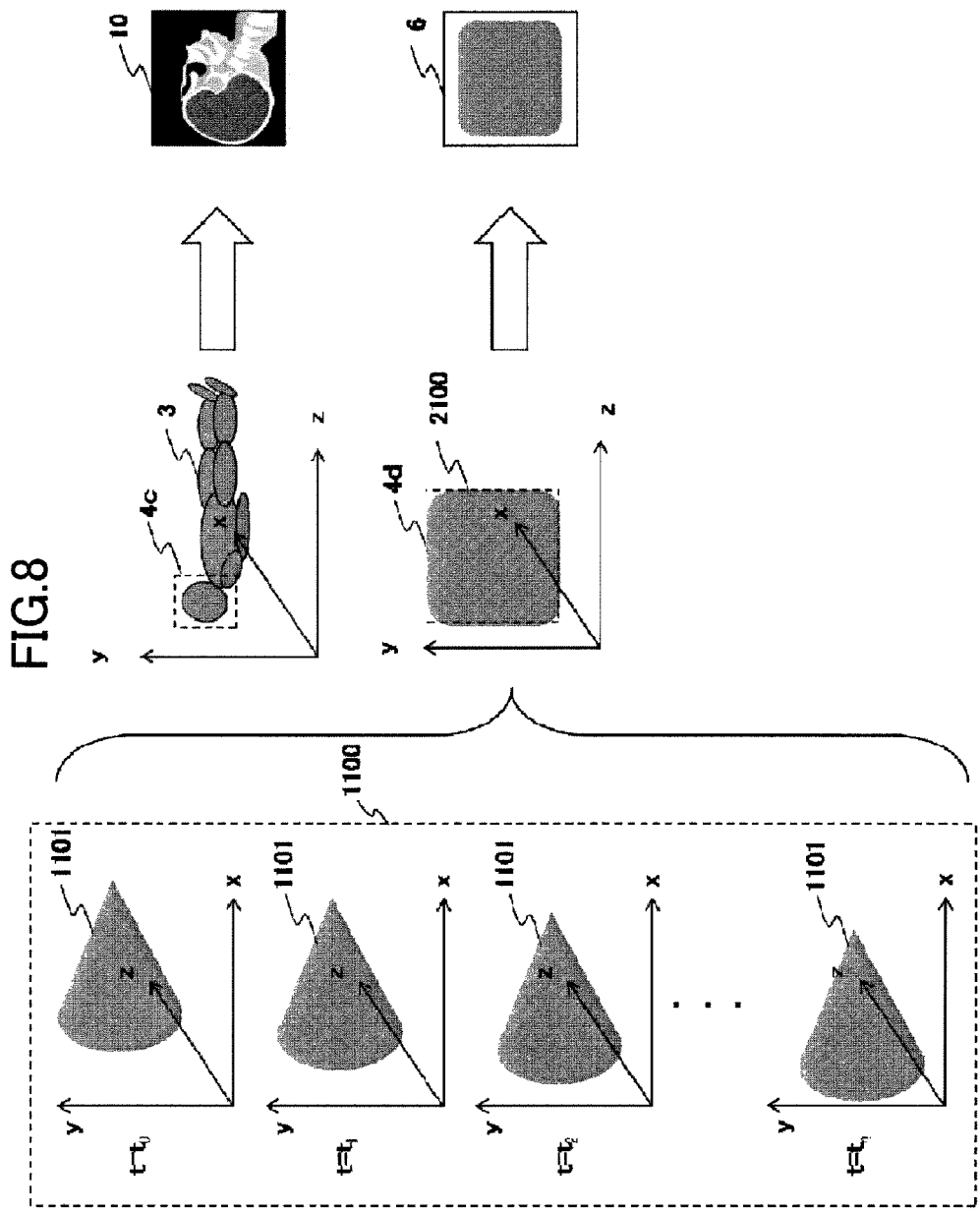
FIG. 8 is a diagram for explaining irradiation dose image generation processing in a second embodiment.

An image of the object 3 in the second embodiment is a scanogram image 10 of the object 3 shown in FIG. 8. A region 4c of the scanning range of the scanogram image 10 is a region parallel to the YZ plane. One or a plurality of scanogram images 10 may be used, and the number of scanogram images 10 is not particularly limited. In addition, the scanogram image 10 may be captured from any direction of the front, plane, left side surface, right side surface, and others of the object 3, or may be captured multiple times by combining a plurality of directions.

Figure 9:
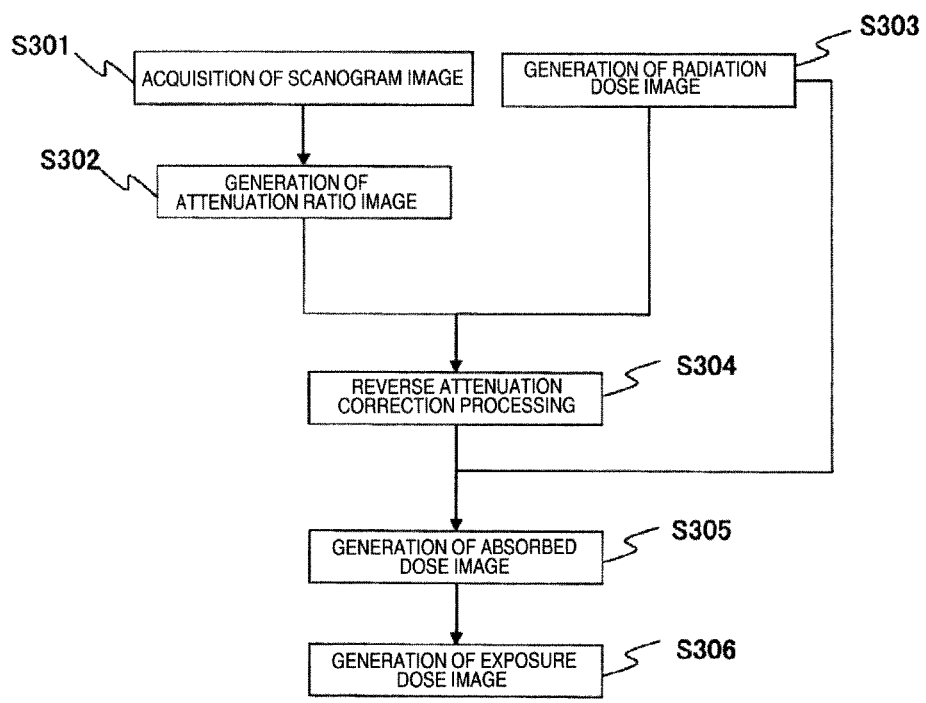
FIG. 9 is a flowchart showing the flow of exposure dose image generation processing in the second embodiment.
Figure 10:
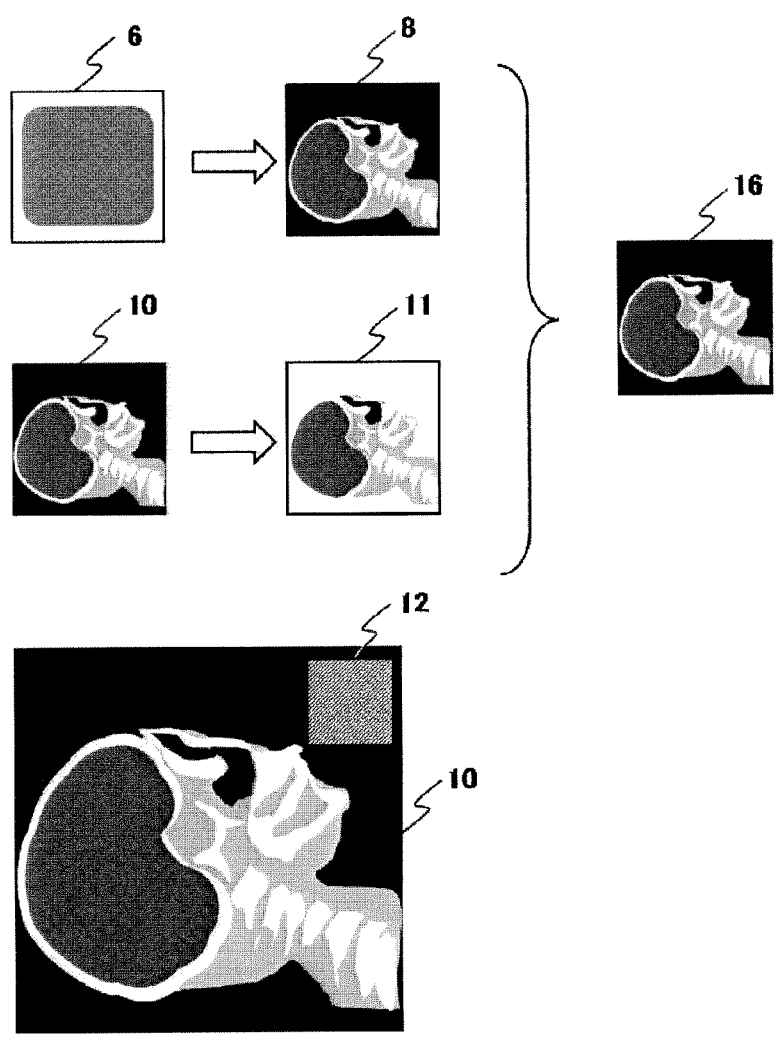
FIG. 10 is a diagram for explaining exposure dose image generation processing in the second embodiment.

As shown in FIG. 9, the image reconstruction device 221 of the X-ray CT apparatus acquires the scanogram image 10 shown in FIG. 4 (S301), and converts the scanogram image 10 into an attenuation ratio image 11 on the basis of the reference attenuation value (S302).

The attenuation ratio image 11 is an image showing the distribution of the attenuation ratio. The attenuation ratio is a value (relative value) indicating the ratio of each pixel value to the reference attenuation value.

The reference attenuation value may be an average pixel value of a part of a region 12 (refer to FIG. 10) of a scanogram image, data measured in advance, or data obtained by a numerical simulation. Although the region 12 of a part of the scanogram image is preferably a region of the air, the region 12 may be a region of a material other than the air.

Then, the image reconstruction device 221 acquires the irradiated X-ray information from the storage device 213 according to the scanning conditions. The image reconstruction device 221 acquires the irradiated X-ray information from the storage device 213 at each time (t=t0, . . . , tn) at predetermined intervals from the start (t=t0) of X-ray irradiation to the end (t=tn) of X-ray irradiation.

The irradiated X-ray information is three-dimensional irradiation intensity distribution data 1101 shown in FIG. 8. In the example shown in FIG. 8, the three-dimensional irradiation intensity distribution data 1101 has the spread (fan angle) of X-ray beams in the slice surface direction (x-y plane direction) and the spread (cone angle) of X-ray beams in the body axis direction (z-axis direction). However, the three-dimensional irradiation intensity distribution data 1101 is not limited to the example shown in FIG. 8.

Then, the image reconstruction device 221 generates two-dimensional irradiation dose data 2100 by performing time integration of a group 1100 of the three-dimensional irradiation intensity distribution data at each time and performing a projective transformation (in the example shown in FIG. 8, a projective transformation from the three dimension to the two dimension in accordance with the scanogram image 10. Then, the image reconstruction device 221 generates a irradiation dose image 6 (a stationary scanning irradiation dose image and an irradiated X-ray image) having the same region 4d as an scanning region 4c of the scanogram image 10 (S303).

Then, the image reconstruction device 221 calculates the amount of attenuation by the object 3 by performing reverse attenuation correction processing on the irradiation dose image 6 using the attenuation ratio image 11 (S304), and generates an absorbed dose image 16 (stationary scanning absorbed dose image) assuming that the amount of attenuation by the object 3 is equivalent to the absorbed amount by the object 3 (S305).

Since the second embodiment is a stationary scanning, forward projection processing and reverse projection processing are not performed. That is, processing equivalent to the projection data generation processing (S203 and S205) and the irradiation dose correction image generation processing (S207) in the first embodiment are not performed.

In the reverse attenuation correction processing in S304, the image reconstruction device 221 generates an absorbed dose image using the expression (2) shown below.

[Expression 2]

$$f_A = (1 - e^{-f_T})f_0 \qquad (2)$$
$$f_T = \ln\left(\frac{kf_t}{f_0}\right)$$
$$k = \frac{\int f_0(x, y)dxdy}{\int f_t(x, y)dxdy}$$

fA: absorbed dose image
f0: irradiation dose image
fT: attenuation ratio image
ft: scanogram image
k: reference attenuation value Then, the image reconstruction device 221 converts the absorbed dose image 16 into an exposure dose image using a dose equivalent conversion factor (S306). For example, the value shown in the recommendations of the ICRP may be used as the dose equivalent conversion factor.

In addition, the display device 211 of the X-ray CT apparatus displays the dose information as in the first embodiment.

As described above, according to the second embodiment, the exposure dose of the object 3 and the irradiation dose for the object 3 according to the scanning conditions can be quickly evaluated in the scanogram imaging (stationary scanning).

In addition, the exposure dose of the object 3 and the irradiation dose for the object 3 can be evaluated and managed with high accuracy and in detail. In addition, since the scanogram imaging is also a stationary scanning, the exposure dose and the irradiation dose can be evaluated and managed in the same manner as in the scanogram imaging.

In the present invention, the physical characteristics reflecting the material configuration of the object 3 and the morphological information included in the object image (clinical image information) are used. Accordingly, even if different things from body tissue, such as things remaining in the body or a contrast agent, or things which significantly attenuate irradiated X-rays are present as the object 3, it is possible to evaluate the exposure dose.

In addition, since a irradiation dose image showing the distribution of the irradiation dose of X-rays irradiated to the object 3 can be provided, it is also possible to evaluate and manage the irradiation dose. Accordingly, conversion into the indices (CTDI, DLP, CTDIw, CTDIvol, and the like) of the exposure dose unique to the known CT examination can be easily performed.

In addition, in the processing shown in S301 to S305 shown in FIG. 9, calculation processing for each organ or the like of the object 3 (for example, processing for calculating the transmission length of an X-ray for each organ or the like) is not performed. Accordingly, since the amount of calculation is reduced even if many organs or the like are present in the image to evaluate the exposure dose, it is possible to shorten the calculation time.

Third Embodiment

Although the evaluation of the exposure dose in each of the tomographic scanning (rotation scanning) and the scanogram imaging (stationary scanning) has been described in the first and second embodiments, a case where both the tomographic scanning (rotation scanning) and the scanogram imaging (stationary scanning) are performed and there is an overlapping region in the scanning range will be described in a third embodiment.

Processing of an X-ray CT apparatus in the third embodiment will be described with reference to FIG. 11.

The X-ray CT apparatus acquires a scanogram image and a tomographic image by performing scanogram imaging and tomographic scanning on the basis of the set scanning conditions.

Then, the image reconstruction device 221 of the X-ray CT apparatus acquires the irradiated X-ray information in the scanogram imaging from the storage device 213 according to the scanning conditions. The image reconstruction device 221 acquires the irradiated X-ray information from the storage device 213 at each time (t=ts0, . . . , tsn) at predetermined intervals from the start (t=ts0) of X-ray irradiation to the end (t=tsn) of X-ray irradiation in the scanogram imaging. The irradiated X-ray information in the scanogram imaging is a group 1100 of three-dimensional irradiation intensity distribution data shown in FIG. 11.

In addition, the image reconstruction device 221 acquires the irradiated X-ray information in the tomographic scanning from the storage device 213 according to the scanning conditions. The image reconstruction device 221 acquires the irradiated X-ray information from the storage device 213 at each time (t=tr0, . . . , trn) at predetermined intervals from the start (t=tr0) of X-ray irradiation to the end (t=trn) of X-ray irradiation in the tomographic scanning. The irradiated X-ray information in the tomographic scanning is a group 1000 of three-dimensional irradiation intensity distribution data shown in FIG. 11.

Then, the image reconstruction device 221 generates cumulative three-dimensional irradiation dose data 2200 by combining both the group 1100 of three-dimensional irradiation intensity distribution data in the scanogram imaging and the group 1000 of three-dimensional irradiation intensity distribution data in the tomographic scanning at each time and performing time integration of the group 1200 of combined three-dimensional irradiation intensity distribution data.

Then, the image reconstruction device 221 sets a region 4e, which is present at the same z position as a region showing the tomographic plane of a tomographic image to be evaluated, as a cut plane, and extracts the pixel value of the cumulative three-dimensional irradiation dose data 2200 in the cut plane and sets the result as a cumulative irradiation dose image 15.

Figure 11:
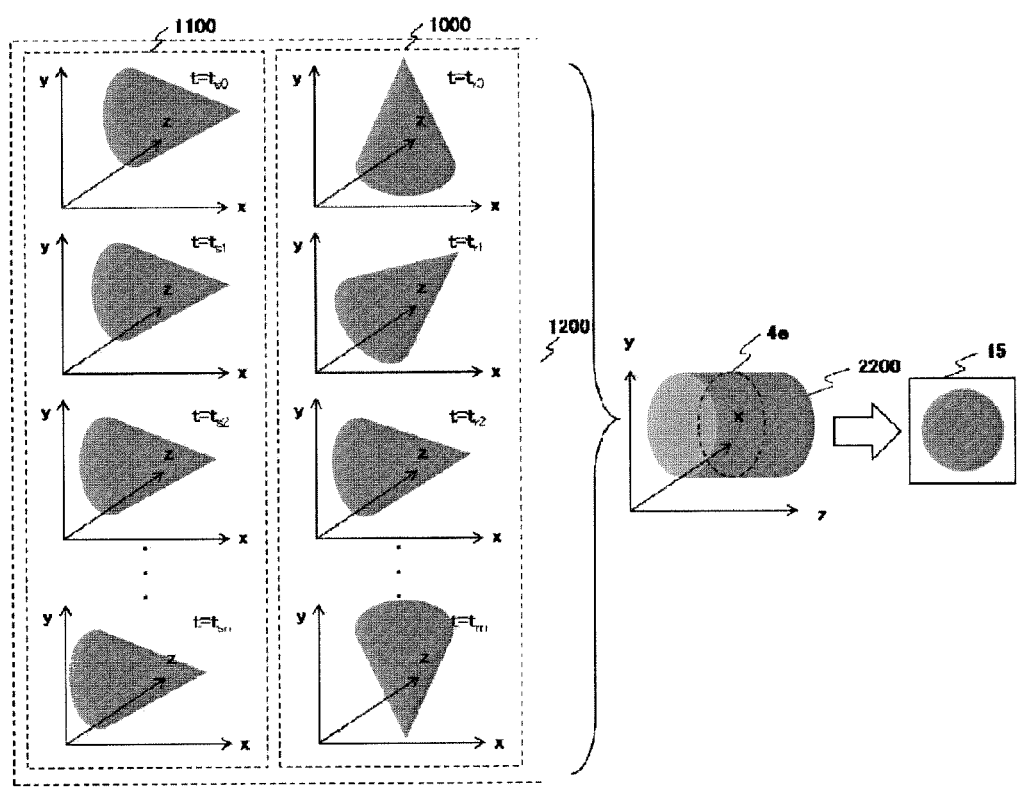
FIG. 11 is a diagram for explaining cumulative irradiation dose image generation processing in a third embodiment.

In addition, although the cumulative irradiation dose image 15 shown in FIG. 11 is expressed such that the pixel value is fixed, the cumulative irradiation dose image 15 has a different pixel value for each pixel in practice. That is, the cumulative irradiation dose image 15 is an image with distribution.

Then, the image reconstruction device 221 generates a cumulative exposure dose image using the tomographic image to be evaluated and the cumulative irradiation dose image 15 as in the first embodiment.

In addition, the display device 211 of the X-ray CT apparatus displays the dose information as in the first embodiment.

As described above, according to the third embodiment, the cumulative exposure dose of the object 3 and the cumulative irradiation dose for the object 3 according to the scanning conditions can be quickly evaluated in the case where both the tomographic scanning (rotation scanning) and the scanogram imaging (stationary scanning) are performed and there is an overlapping region in the scanning range.

In addition, the cumulative exposure dose of the object 3 and the cumulative irradiation dose for the object 3 can be evaluated and managed with high accuracy and in detail.

Fourth Embodiment

Although combining the three-dimensional irradiation intensity distribution data in the scanogram imaging and the three-dimensional irradiation intensity distribution data in the tomographic scanning and evaluating the cumulative exposure dose and the cumulative irradiation dose have been described in the third embodiment, combining exposure dose images will be described in a fourth embodiment.

Processing of an X-ray CT apparatus in the fourth embodiment will be described with reference to FIG. 12.

The X-ray CT apparatus acquires a scanogram image and a tomographic image by performing scanogram imaging and tomographic scanning on the basis of the set scanning conditions.

Then, the image reconstruction device 221 of the X-ray CT apparatus generates a tomographic scanning exposure dose image 9c in the same manner as described in the first embodiment. The tomographic scanning exposure dose images 9c at a plurality of slice positions (z positions) are shown in FIG. 12.

Then, the image reconstruction device 221 generates a scanogram imaging exposure dose image 9d in the same manner as described in the second embodiment. The scanogram imaging exposure dose image 9d shown in FIG. 12 is an image showing the exposure dose of scanogram imaging captured from the front direction of the object 3.

Then, the image reconstruction device 221 generates exposure dose data 13 per unit thickness (thickness means a slice thickness) by projecting the tomographic scanning exposure dose image 9c in the scanning direction of the scanogram imaging. In the graph of the exposure dose data 13 shown in FIG. 12, the horizontal axis indicates the position of the object 3 in the body width direction (x direction) and the vertical axis indicates the exposure dose per unit thickness.

Then, the image reconstruction device 221 generates a cumulative exposure dose image by adding each item of the exposure dose data 13 to a corresponding slice position 14 of the scanogram imaging exposure dose image 9d.

In addition, the display device 211 of the X-ray CT apparatus displays the dose information as in the first embodiment.

As described above, according to the fourth embodiment, the cumulative exposure dose of the object 3 according to the scanning conditions can be quickly evaluated by combining a plurality of exposure dose images.

In addition, the cumulative exposure dose of the object 3 can be evaluated and managed with high accuracy and in detail.

Although the image reconstruction device 221 of the X-ray CT apparatus generates the irradiation dose image, the exposure dose image, or the like in the first to fourth embodiments described above, the present invention is not limited to this.

For example, instead of the image reconstruction device 221, a CPU (control unit) of a computer (medical image processing apparatus) that performs medical image processing may generate the irradiation dose image, the exposure dose image, or the like. In this case, the medical image processing apparatus acquires the scanning conditions, information which is a basis for a reconstructed image of an object, and the like from the X-ray CT apparatus. For example, the X-ray CT apparatus may transmit such information to the medical image processing apparatus through a network. In addition, for example, the X-ray CT apparatus may store such information in a storage medium, and the medical image processing apparatus may read such information from the storage medium.

In addition, in this case, the medical image processing apparatus stores three-dimensional irradiation intensity distribution data (irradiated X-ray information) in a storage device (storage unit) for each scanning condition.

In addition, the control unit of the medical image processing apparatus acquires the irradiated X-ray information from the storage unit according to the scanning conditions, and generates an exposure dose image on the basis of the irradiated X-ray information and the reconstructed image of the object. In addition, the display device (display unit) of the medical image processing apparatus displays dose information, such as the exposure dose image.

While the preferred embodiments of the X-ray CT apparatus according to the present invention have been described with reference to the accompanying drawings, the present invention is not limited to such examples. It is apparent to those skilled in the art that various changes and modifications can be made within the range of the technical idea disclosed in this specification, and it should be understood undoubtedly that they also belong to the technical range of the present invention.

REFERENCE SIGNS LIST

1: scanning means
2: operating means
3: object
4a, 4b, 4c, 4d, 4e: region
5: tomographic image
6: irradiation dose image
7: attenuation coefficient image
8: irradiation dose correction image
9a: exposure dose image of a coronal image
9b: exposure dose image of an axial image
9c: tomographic scanning exposure dose image
9d: scanogram imaging exposure dose image
10: scanogram image
11: attenuation ratio image
12: region of a part of a scanogram image
13: exposure dose data
14: slice position
15: cumulative irradiation dose image
16: absorbed dose image
50: attenuation coefficient projection data
51: irradiation dose projection data
52: attenuation correction irradiation dose projection data
100: gantry
101: bed
102: X-ray generator
103: X-ray detector
104: collimator device
105: high voltage generator
106: data collection device
107: driving device
200: central control device
201: input/output device
202: calculation device
211: display device
212: input device
213: storage device
221: image reconstruction device
222: image processing device
700: dose management screen
701: irradiation range image
702: exposure dose according to scanning
703: exposure dose index conversion button
704: irradiation dose according to scanning
705: exposure dose according to a part
705a: exposure dose of abdomen
706: exposure dose according to an organ
706a: exposure dose of lung
706b: exposure dose of liver
706c: exposure dose of spine
707a: ROI
707b: exposure dose in ROI
707: exposure dose in ROI
708: ON/OFF button of display on an image
1000, 1100: group of three-dimensional irradiation intensity distribution data
1001, 1101: three-dimensional irradiation intensity distribution data
1200: group of combined three-dimensional irradiation intensity distribution data
2000: three-dimensional irradiation dose data
2100: two-dimensional irradiation dose data
2200: cumulative three-dimensional exposure dose data

The invention claimed is:

1. An X-ray CT apparatus comprising:
an X-ray irradiation unit that irradiates X-rays from periphery of an object;
an X-ray detection unit that detects X-rays transmitted through the object as X-ray information;
an image reconstruction unit that generates a reconstructed image of the object from the X-ray information and that, according to scanning conditions, acquires an irradiated X-ray image which is a distribution of an irradiation intensity of X-rays irradiated to the object by the X-ray irradiation unit, performs projection conversion of the irradiated X-ray image and the reconstructed image, and generates an exposure dose image, which is an image showing a distribution of an exposure dose of the object, and also calculates the exposure dose using the projection-converted reconstructed image and an irradiated X-ray image corresponding to a generation region of the reconstructed image; and
a display unit that displays the exposure dose image and the exposure dose,
wherein the image reconstruction unit generates irradiation dose data by performing time integration of the irradiated X-ray image at each time at predetermined intervals from start of irradiation to end of irradiation, and generates an image, which shows a distribution of a dose of X-rays irradiated to the object, on the basis of the irradiation dose data,
wherein the image reconstruction unit generates an attenuation coefficient image, which is an image showing a distribution of an attenuation coefficient, by converting a CT value of the reconstructed image into an attenuation coefficient on the basis of information indicating a relationship between the CT value and the attenuation coefficient, and wherein the image reconstruction unit generates projection data of the attenuation coefficient image and projection data of the irradiation dose image by performing forward projection processing, which is a transformation from a Cartesian coordinate system to a projection coordinate system, on the attenuation coefficient image and the irradiation dose image, and generates an irradiation dose correction image, which is an image showing a reduction result of the amount of attenuation with respect to the irradiation dose image, by performing reverse attenuation correction processing on the projection data of the irradiation dose image using the projection data of the attenuation coefficient image and performing reverse projection processing, which is a transformation from the projection coordinate system to the Cartesian coordinate system, on projection data of the irradiation dose image after the reverse attenuation correction processing.

2. The X-ray CT apparatus according to claim 1, wherein the image reconstruction unit generates a cumulative exposure dose image, which is an image showing a distribution of a cumulative exposure dose of the object, on the basis of a plurality of the exposure dose images.

3. The X-ray CT apparatus according to claim 1, wherein the display unit displays the irradiation dose image so as to overlap another image of the object.

4. The X-ray CT apparatus according to claim 1, wherein the image reconstruction unit generates a cumulative irradiation dose image, which is an image showing a distribution of a dose of X-rays irradiated to the object in rotation scanning and stationary scanning, by performing time integration of the irradiated X-ray information regarding rotation scanning and stationary scanning of the irradiated X-ray information.

5. The X-ray CT apparatus according to claim 1, wherein the image reconstruction unit generates a stationary scanning irradiation dose image, which is an image showing a distribution of a dose of X-rays irradiated to the object in stationary scanning, by performing time integration of the irradiated X-ray information regarding stationary scanning of the irradiated X-ray information.

6. The X-ray CT apparatus according to claim 1, wherein the image reconstruction unit calculates one of CTDI, DLP, CTDIw, and CTDIvol on the basis of the irradiation dose image.

7. The X-ray CT apparatus according to claim 6, wherein the image reconstruction unit generates an absorbed dose image, which is an image showing a distribution of a dose of X-rays absorbed into the object, on the basis of a difference between the irradiation dose image and the irradiation dose correction image.

8. The X-ray CT apparatus according to claim 7, wherein the image reconstruction unit calculates an exposure dose for each organ and/or tissue by identifying a region of an organ and/or tissue in the reconstructed image and collating the region with the absorbed dose image.

9. The X-ray CT apparatus according to claim 8, wherein the display unit displays the exposure dose for each organ and/or tissue.

10. The X-ray CT apparatus according to claim 7, wherein the image reconstruction unit calculates an exposure dose for each part by identifying a region of each part in the reconstructed image and collating the region with the absorbed dose image.

11. The X-ray CT apparatus according to claim 10, wherein the display unit displays the exposure dose for each part.

12. An X-ray CT apparatus comprising:
an X-ray irradiation unit that irradiates X-rays from periphery of an object;
an X-ray detection unit that detects X-rays transmitted through the object as X-ray information;
an image reconstruction unit that generates a reconstructed image of the object from the X-ray information and that, according to scanning conditions, acquires an irradiated X-ray image which is a distribution of an irradiation intensity of X-rays irradiated to the object by the X-ray irradiation unit, performs projection conversion of the irradiated X-ray image and the reconstructed image, and generates an exposure dose image, which is an image showing a distribution of an exposure dose of the object, and also calculates the exposure dose using the projection-converted reconstructed image and an irradiated X-ray image corresponding to a generation region of the reconstructed image; and
a display unit that displays the exposure dose image and the exposure dose,
wherein the image reconstruction unit generates irradiation dose data by performing time integration of the irradiated X-ray image at each time at predetermined intervals from start of irradiation to end of irradiation, and generates an image, which shows a distribution of a dose of X-rays irradiated to the object, on the basis of the irradiation dose data,
wherein the image reconstruction unit generates an attenuation coefficient image, which is an image showing a distribution of an attenuation coefficient, by converting a CT value of the reconstructed image into an attenuation coefficient on the basis of information indicating a relationship between the CT value and the attenuation coefficient, and
wherein the image reconstruction unit generates an attenuation ratio image, which is an image showing a distribution of an attenuation ratio, from a stationary scanning image on the basis of information indicating a reference attenuation value, and generates a stationary scanning absorbed dose image, which is an image showing a distribution of a dose of X-rays absorbed into the object in stationary scanning, by performing reverse attenuation correction processing on the stationary scanning irradiation dose image using the attenuation ratio image.

13. The X-ray CT apparatus according to claim 12, wherein the image reconstruction unit generates a cumulative exposure dose image, which is an image showing a distribution of a cumulative exposure dose of the object, on the basis of a plurality of the exposure dose images.

14. The X-ray CT apparatus according to claim 12, wherein the display unit displays the irradiation dose image so as to overlap another image of the object.

15. The X-ray CT apparatus according to claim 12, wherein the image reconstruction unit generates a cumulative irradiation dose image, which is an image showing a distribution of a dose of X-rays irradiated to the object in rotation scanning and stationary scanning, by performing time integration of the irradiated X-ray information regarding rotation scanning and stationary scanning of the irradiated X-ray information.

16. The X-ray CT apparatus according to claim 12, wherein the image reconstruction unit generates a stationary scanning irradiation dose image, which is an image showing a distribution of a dose of X-rays irradiated to the object in stationary scanning, by performing time integration of the irradiated X-ray information regarding stationary scanning of the irradiated X-ray information.

17. The X-ray CT apparatus according to claim 12, wherein the image reconstruction unit calculates one of CTDI, DLP, CTDIw, and CTDIvol on the basis of the irradiation dose image.

* * * * *